(12) United States Patent
Hancock

(10) Patent No.: US 7,374,751 B1
(45) Date of Patent: May 20, 2008

(54) QS-21 AND IL-12 AS AN ADJUVANT COMBINATION

(75) Inventor: Gerald E. Hancock, Honeoye Falls, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 612 days.

(21) Appl. No.: 10/311,422

(22) PCT Filed: Jun. 21, 2001

(86) PCT No.: PCT/US01/19805

§ 371 (c)(1),
(2), (4) Date: Dec. 16, 2002

(87) PCT Pub. No.: WO01/97841

PCT Pub. Date: Dec. 27, 2001

(51) Int. Cl.
*A61K 39/39* (2006.01)
*A61K 39/12* (2006.01)
*A61K 39/02* (2006.01)
*A61K 45/00* (2006.01)
*A01N 65/00* (2006.01)

(52) U.S. Cl. ............... 424/85.2; 424/204.1; 424/206.1; 424/211.1; 424/234.1; 424/283.1; 424/725

(58) Field of Classification Search ............. None
See application file for complete search history.

(56) References Cited

U.S. PATENT DOCUMENTS

| | | | |
|---|---|---|---|
| 4,912,094 A * | 3/1990 | Myers et al. | 514/54 |
| 5,057,540 A * | 10/1991 | Kensil et al. | 424/278.1 |
| 5,723,130 A * | 3/1998 | Hancock et al. | 424/211.1 |
| 6,071,893 A * | 6/2000 | Graham et al. | 514/44 |
| 6,375,945 B1 * | 4/2002 | Boon et al. | 424/85.2 |
| 6,514,503 B1 * | 2/2003 | Gizurarson et al. | 424/278.1 |
| 6,929,794 B1 * | 8/2005 | Mills et al. | 424/184.1 |

FOREIGN PATENT DOCUMENTS

| | | |
|---|---|---|
| WO | WO9610423 A | 4/1996 |
| WO | WO9611019 A | 4/1996 |
| WO | WO9940937 A | 8/1999 |

OTHER PUBLICATIONS

Schoenhaut et al., J Immunol Jun. 1, 1992;148(11):3433:40.*
Silla et al., European Cytokine Network Jun. 1999 10(2):181-90.*
Singh et al.,Nat Biotechnol. Nov. 1999;17(11):1075-81.*
Yoshida et al., (Mol Cell Biochem. Jun. 7, 1996;159(1):73-80. Abstract Only.*
Abd-Elfattah et al., Ann Thorac Surg Nov. 1999;68(5):1954-9.*
Dertzbaugh, Plasmid 1998;39(2):100-13, Review.*
Laver et al., Cell. May 18, 1990; 61:553-556.*
Barlow et al., Nature. Aug. 21, 1986; 33:747-748.*
Weinberg et al., J Immunol Jan. 1, 1988;140(1):294-9.*
Datta et al, Immunol Rev Jun. 2004;199:217-26, Abstract Only.*
Silla, et al., "Enhancement by IL-12 of the cytolytic T lymphocyte (CTL) response of mice immunized with tumor-specific peptides in an adjuvant containing QS21 and MPL," European Cytokine Network, 10(2):181-189 (1999).
Hancock, et al., "QS-21 synergizes with recombinant interleukin-12 to create a potent adjuvant formulation for the fusion protein of respiratory syncytial virus," Viral Immunology, 13(4):503-509 (2000).

* cited by examiner

*Primary Examiner*—Manjunath Rao
*Assistant Examiner*—Cherie Woodward
(74) *Attorney, Agent, or Firm*—Michael J. Moran (57) ABSTRACT

Adjuvant compositions comprising an effective amount IL-12 and QS-21 are disclosed. Immunogenic, vaccine and pharmaceutical compositions comprising a mixture of antigen and an adjuvant composition comprising an effective amount of IL-12 and QS-21 are also disclosed. These compositions elicit functional cell-mediated and humoral immune responses against at least one antigen. Methods of using the disclosed compositions are also disclosed.

20 Claims, 6 Drawing Sheets

SEQUENCE LISTING

```
<160> NUMBER OF SEQ ID NOS: 2

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 28
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25
```

QS-21 AND IL-12 AS AN ADJUVANT COMBINATION

BACKGROUND OF THE INVENTION

IL-12 is a heterodimeric cytokine that is primarily produced by dendritic cells, macrophages and neutrophils and plays an essential role in the generation of type 1 immune responses and cell-mediated immunity (Brunda, *J. Leukocyte Biol.* 55:280-288 (1994); Scott and Trinchieri, *Semin. Immunol.* 9:285-291 (1997)). The results from several studies in a variety of animal models support the idea that rIL-12 has great promise as an adjuvant for prophylactic or therapeutic vaccines against infectious and metastatic diseases (Rodolfo and Colombo, *Methods* 19:114-120 (1999); Scott and Trinchieri, *Semin. Immunol.* 9:285-291 (1997)). Recently, it was reported that rIL-12 has the potential to serve as an adjuvant for natural F protein of RSV (Hancock et al. *Viral Immunol.* 13:57-72 (2000)). In BALB/c mice, the results suggested that rIL-12 enhanced the capacity of F protein, when adsorbed to aluminum hydroxide adjuvant (F/AlOH), to elicit T cell responses that were more balanced and not polarized towards a type 2 phenotype. However, co-formulation with rIL-12 did not completely regulate all type 2 responses elicited by F/AlOH. That is, upon challenge of mice primed with F/AlOH plus rIL-12, IL-5-dependent pulmonary eosinophilia was still observed. Furthermore, the data from recent phase I clinical trials (Atkins et al. *Clin. Cancer Res.* 3:409-417 (1997)) also suggest that high doses of rIL-12 may be too reactogenic for use in routine vaccination.

The ability of the highly purified saponin QS-21 (Kensil et al., *J. Immunol.* 146:431-437 (1991)) to improve the quality and quantity of immune responses to F protein has been reported (Hancock et al., *Vaccine* 13:391-400 (1995); Hancock et al., *J. Virol.* 70:7783-7791 (1996)). Compared to F/AlOH, vaccination of naïve mice with F/QS-21 resulted in the generation of augmented serum neutralizing titers that were associated with a shift in F protein-specific Ig production from the predominant G1 to G2a subclass. Upon challenge there was also an increase antigen dependent killer cell activity mediated by MHC class I restricted CD8$^+$T cells and protein-specific antibody secreting cells in the lungs. Importantly, there was a significant reduction in IL-5-dependent pulmonary eosinophilia. However, clinical data has implied that QS-21 in this formulation was associated with local acute toxicity immediately after injection.

SUMMARY OF THE INVENTION

The invention relates to an adjuvant composition comprising an effective amount of QS-21 and IL-12 and an optional physiologically acceptable vehicle. The invention also relates to an adjuvant composition comprising an effective amount of QS-21 and L-12 and an optional physiologically acceptable vehicle, wherein the composition does not comprise substantial 3-O-deacylated monophosphoryl lipid A. The invention further relates to an adjuvant composition comprising an effective amount of QS-21 and IL-12 and an optional physiologically acceptable vehicle, wherein the composition comprises less than about 1 µg of 3-O-deacylated monophosphoryl lipid A, more preferably less than about 0.5 µg of 3-O-deacylated monophosphoryl lipid A, and even more preferably less than about 0.0001 µg (1 Ug) of 3-O-deacylated monophosphoryl lipid A. In a preferred embodiment, the adjuvant composition contains no 3-O-deacylated monophosphoryl lipid A. The invention also relates to an adjuvant composition comprising an effective amount of QS-21 and IL-12 and an optional physiologically acceptable vehicle, wherein the composition comprises less than about 0.05 µg of IL-12. In one embodiment, the invention relates to an adjuvant composition consisting essentially of an effective amount of QS-21 and IL-12 and an optional physiologically acceptable vehicle.

In particular embodiments of the invention, the QS-21 is present in an amount which does not engender substantial local toxicity when administered to a vertebrate. In other embodiments of the invention, the IL-12 is present in an amount which is not substantially reactogenic when administered to a vertebrate. In preferred embodiments of the invention, the QS-21 is present in an amount which does not engender substantial local toxicity when administered to a vertebrate, and the IL-12 is present in an amount which is not substantially reactogenic when administered to a vertebrate. Preferably the adjuvant composition will comprise an effective amount of QS-21 and IL-12. As used herein, an effective amount of QS-21 and IL-12 is an amount which allows the use of a decreased amount of either QS-21 or IL-12 or both QS-21 and IL-12, relative to the amount of each component in the absence of the other which is required for a similar immunological effect, while maintaining the adjuvant activity of the composition. In preferred embodiments of the invention, the IL-12 is present in an amount of from about 0.01 ng to about 50 µg. In other preferred embodiments, the QS-21 is present in an amount of from about 0.01 ng to about 50 µg. Preferably, the combination of QS-21 and IL-12 produce a synergistic adjuvant effect. In one embodiment of the invention, the IL-12 is recombinant human IL-12.

The invention further relates to an immunogenic composition comprising at least one antigen and an adjuvant composition comprising an effective amount of IL-12 and QS-21. The invention also relates to an immunogenic composition comprising at least one antigen and an adjuvant composition comprising an effective amount of QS-21 and IL-12, wherein the adjuvant composition does not comprise substantial 3-O-deacylated monophosphoryl lipid A. The invention is also drawn to an immunogenic composition comprising at least one antigen and an adjuvant composition comprising an effective amount of QS-21 and IL-12, wherein the adjuvant composition comprises less than about 1 µg of 3-O-deacylated monophosphoryl lipid A, more preferably less than about 0.5 µg of 3-O-deacylated monophosphoryl lipid A and even more preferably less than about 0.0001 µg (1 Ug) 3-O-deacylated monophosphoryl lipid A. In a preferred embodiment, the adjuvant composition contains no 3-O-deacylated monophosphoryl lipid A. The invention is also drawn to an immunogenic composition comprising at least one antigen and an adjuvant composition comprising an effective amount of QS-21 and IL-12, wherein the composition comprises less than about 0.05 µg of IL-12. In one embodiment, the invention relates to an immunogenic composition comprising at least one antigen and an adjuvant composition consisting essentially of an effective amount of QS-21 and IL-12 and an optional physiologically acceptable vehicle.

In particular embodiments of the immunogenic compositions, the QS-21 is present in an amount which does not engender substantial local toxicity when administered to a vertebrate. In other embodiments of the invention, the IL-12 is present in an amount which is not substantially reactogenic when administered to a vertebrate. In preferred embodiments of the invention the QS-21 is present in an amount which does not engender substantial local toxicity when administered to a vertebrate, and the IL-12 is present in an amount which is not substantially reactogenic when administered to a vertebrate. In preferred embodiments of the invention, the IL-12 is present in an amount of from about 0.01 ng to about 50 µg. In other preferred embodiments, the QS-21 is present in an amount of from about 0.01 ng to about 50 µg. Preferably, the QS-21 and IL-12 produce a synergistic adjuvant effect. In one embodiment of the invention, the IL-12 is recombinant human IL-12. In one embodiment of the invention, the antigen is a viral antigen. In a preferred embodiment, the antigen is respiratory syncytial virus F protein or functional portion thereof. In another embodiment, the antigen is a bacterial antigen. In that embodiment, the preferred antigen is P4 protein, or functional portion thereof, from non-typable *Haemophilus influenzae*.

The invention also relates to a method of eliciting an immune response to an antigen, comprising administering to a vertebrate an immunologically effective amount of a composition comprising at least one antigen and an adjuvant composition comprising an effective amount of QS-21 and IL-12, thereby eliciting an immune response to the antigen in the vertebrate. The invention further relates to a method of eliciting an immune response to an antigen, comprising administering to a vertebrate an immunologically effective amount of a composition comprising at least one antigen and an adjuvant composition comprising an effective amount of QS-21 and IL-12, wherein the composition does not comprise substantial 3-O-deacylated monophosphoryl lipid A, thereby eliciting an immune response to the antigen in the vertebrate. The invention also pertains to a method of eliciting an immune response to an antigen, comprising administering to a vertebrate an immunologically effective amount of a composition comprising at least one antigen and an adjuvant composition comprising an effective amount of QS-21 and IL-12, wherein the composition comprises less than about 1 µg of 3-O-deacylated monophosphoryl lipid A, preferably less than about 0.5 µg of 3-O-deacylated monophosphoryl lipid A, and more preferably less than about 0.0001 µg (1 Ug) 3-O-deacylated monophosphoryl lipid A, thereby eliciting an immune response to the antigen in the vertebrate. The invention further pertains to a method of eliciting an immune response to an antigen, comprising administering to a vertebrate an immunologically effective amount of a composition comprising at least one antigen and an adjuvant composition comprising an effective amount of QS-21 and IL-12, wherein the composition comprises less than about 0.05 µg of IL-12, thereby eliciting an immune response to the antigen in the vertebrate. In one embodiment, the invention relates to a method of eliciting an immune response to an antigen, comprising administering to a vertebrate an immunologically effective amount of a composition comprising at least one antigen and an adjuvant composition consisting essentially of an effective amount of QS-21 and IL-12 and an optional physiologically acceptable vehicle.

In particular embodiments of the method, the QS-21 is present in an amount which does not engender substantial local toxicity when administered to a vertebrate. In other embodiments of the invention, the IL-12 is present in an amount which is not substantially reactogenic when administered to a vertebrate. In preferred embodiments of the invention, the QS-21 is present in an amount which does not engender substantial local toxicity when administered to a vertebrate, and the IL-12 is present in an amount which is not substantially reactogenic when administered to a vertebrate.

In preferred embodiments of the invention, the IL-12 is present in an amount of from about 0.01 ng to about 50 µg. In other preferred embodiments, the QS-21 is present in an amount of from about 0.01 ng to about 50 µg. Preferably, the QS-21 and IL-12 produce a synergistic adjuvant effect. In one embodiment of the invention, the IL-12 is recombinant human IL-12. In one embodiment of the invention, the antigen is a viral antigen. In a preferred embodiment, the antigen is respiratory syncytial virus F protein or functional portion thereof. In another embodiment, the antigen is a bacterial antigen. In that embodiment, the preferred antigen is P4 protein, or functional portion thereof, from non-typable *Haemophilus influenzae*. In one embodiment, the immune response comprises a response selected from the group consisting of a humoral response, a cell-mediated response, or both a humoral and cell-mediated response.

BRIEF DESCRIPTION OF THE DRAWINGS

In FIGS. 1A-1E, F protein was prepared with 1.0 µg rIL-12 per dose (filled circles) or PBS alone (open circles). The vaccines were co-formulated with 20.0 (FIG. 1A), 4.0 (FIG. 1B), 0.8 (FIG. 1C), or 0.0 (FIG. 1D) µg QS-21 per dose. Control mice (FIG. 1E) were injected with QS-21 (20 µg) in PBS alone (open squares), or experimentally infected (~2×10$^6$ pfu) with the A2 strain of RSV (open triangles). FIG. 1F depicts a separate experiment in which F protein was prepared in PBS alone or with 0.8 µg QS-21 and descending doses (1.0 to 0.01 µg) of rIL-12. Effector cells were tested against RSV-infected (solid lines or filled bars) and control (dashed lines or open bars) syngeneic target cells for antigen dependent killer cell activity; the effector to target ratio was 100:1.

DETAILED DESCRIPTION OF THE INVENTION

Protective immunity induced by vaccination is dependent on the capacity of the vaccine to elicit the appropriate immune response to resist or eliminate the pathogen. Depending on the pathogen, this may require a cell-mediated and/or humoral immune response. The current paradigm for the role of the helper T cells in the immune response is that T cells can be separated into subsets on the basis of the cytokines they produce, and that the distinct cytokine profile observed in these cells determines their function. This T cell model includes two major subsets: Th1 cells that produce IL-2 and interferon-γ (IFN-γ) which augment both cellular and humor immune responses, and Th2 cells that produce IL-4, IL-5 and IL-10 which augment humoral immune responses (Mosmann et al., *J. Immunol.* 126:2348 (1986)). It is often desirable to enhance the immunogenic potency of an antigen in order to obtain a stronger immune response in the organism being immunized, orient the immune response toward a particular type of response, and strengthen host resistance to the antigen-bearing agent. A substance that enhances the immunogenicity of an antigen with which it is administered is known as an adjuvant.

The results from several studies in a variety of animal models support the idea that recombinant IL-12 (rIL-12) has promise as an adjuvant for prophylactic or therapeutic vaccines against infectious and metastatic diseases (Rodolfo and Colombo, *Methods* 19:114-120 (1999); Scott and Trinchieri, *Semin. Immunol.* 146:431-427 (1991)). The ability of IL-12 to improve the quality and quantity of immune responses to RSV F protein has been reported (Hancock et al., *Vaccine* 13:391-400 (1995); Hancock et al., J. Virol 70:7783-7791 (1996)).

Work described herein indicates that QS-21 can synergize with IL-12 and enable elicitation of systemic humoral and cell-mediated immune responses. Thus, IL-12 and QS-21 together from a potent adjuvant combination for eliciting functional cell-mediated and humoral immune responses against antigens. This synergy allows a reduction in the total adjuvant amount and/or a reduction in the amount of either adjuvant component which may have undesirable effects when used alone.

The adjuvant composition will comprise an effective amount of QS-21 and IL-12. As used herein, an effective amount of QS-21 is an amount which permits the use of a reduced amount of IL-12 in the composition while maintaining the adjuvant activity (e.g., elicitation of a humoral response, elicitation of a cytotoxic T lymphocyte (CTL) response or elicitation of both a humoral response and a CTL response) of the adjuvant composition with respect to at least one antigen. An effective amount of IL-12 is an amount which permits the use of a reduced amount of QS-21 in the composition while maintaining the adjuvant activity (e.g., elicitation of a humoral response, elicitation of a CTL response or elicitation of both a humoral response and a CTL response) of the adjuvant composition with respect to at least one antigen. As used herein, an effective amount of QS-21 and IL-12 is an amount which allows the use of a decreased amount of either QS-21 or IL-12 or both QS-21 and IL-12, relative to the amount of each component in the absence of the other which is required for a similar immunological effect with respect to at least one antigen, while maintaining the adjuvant activity of the component.

The effective amount can be additive or synergistic; however, preferably the effective amount is synergistic. That is, the additive or synergistic effects of the combination of IL-12 and QS-21 allow the use of amounts of IL-12, QS-21 or both L-12 and QS-21 which might not be considered to be optimal for eliciting the desired immune response. As used herein, a synergistic effect of the combined adjuvants (QS-21 and IL-12) is an effect which is greater than the sum of the IL-12 adjuvant effect, particularly at the level used in the adjuvant composition, and the QS-21 adjuvant effect, particularly at the level used in the adjuvant composition, when used individually. Use of reduced amounts of IL-12, QS-21 or both IL-12 and QS-21 can be beneficial in reducing the adverse effects such as toxicity and reactogenicity which may be associated with higher doses of IL-12 and QS-21. Effective amounts of QS-21 and IL-12 can be determined by dose curve experiments which utilize a specified reduced dose of one adjuvant and monitor the effects of increasing amounts of the second adjuvant while the desired adjuvant activity is maintained.

In preferred embodiments the IL-12 is present in an amount which is not substantially reactogenic in a mammal to whom the adjuvant composition is administered. That is, IL-12 will preferably be present in the composition in an amount which does not engender an unacceptable response in a mammal to whom the composition is administered. In a preferred embodiment, IL-12 is present in an amount which does not produce substantial fever, nausea, vomiting, oral stomatitis, abnormal liver function tests, lymphopenia, anemia, neutropenia, hyperglycemia, thrombocytopenia and/or hypoalbuminemia. In one embodiment, IL-12 is present in an amount of from about 0.01 ng to about 50 μg. For example, IL-12 can be present in an amount of from about 0.01 ng to about 35 μg, or of from about 0.01 ng to about 20 μg, or of from about 0.01 ng to about 15 μg, or of from about 0.01 ng to about 10 μg, or of from about 0.01 ng to about 5 μg. In a particular embodiment, IL-12 is present in an amount of from about 0.01 μg to about 1.0 μg. In one embodiment, IL-12 is present in an amount less than about 0.05 μg. The particular dosage will depend upon the age, weight and medical condition of the mammal to be treated, as well as on the method of administration and the antigen. Suitable doses will be readily determined by the skilled artisan in accordance with the guidance provided herein.

IL-12 can be obtained from any suitable source. Preferably, the IL-12 is recombinant IL-12 (rIL-12), i.e., it can be produced by recombinant DNA methodology; for example, the gene encoding human IL-12 has been cloned and expressed in host systems, permitting the production of large quantities of pure human IL-12. Also useful in the present invention are biologically active subunits or fragments of IL-12. Further, certain T lymphocyte lines product high levels of IL-12, thus providing a readily available source. Commercial sources of recombinant human and murine IL-12 include Genetics Institute, Inc. (Cambridge, Mass.) (see also published International Patent Application WO 90/05147).

QS-21 is a saponin which is purified from a crude *Quillaja saponaria* extract and has been described by Kensil and Marciani (U.S. Pat. No. 5,057,540). In preferred embodiments of the invention QS-21 is present in the composition in an amount which does not engender substantial local toxicity in a mammal to whom the composition is administered. In particular embodiments, QS-21 is present in the composition in an amount of less than about 50 μg, and more preferably less than about 20 μg. In preferred embodiments, QS-21 is present in the composition in an amount of less than 10 μg, more preferably less than about 4 μg, and even more preferably less than about 1 μg. For example, QS-21 can be present in an amount of from about 0.01 ng to about 35 μg, or of from about 0.01 ng to about 20 μg, or of from about 0.01 ng to about 15 μg, or of from about 0.01 ng to about 10 μg, or of from about 0.01 ng to about 5 μg. In one embodiment, QS-21 is present in an amount of about 0.8 μg or less.

The invention further relates to immunogenic, vaccine or pharmaceutical compositions comprising the adjuvant composition described herein and one or more antigens, along with an optional physiologically or pharmaceutically acceptable vehicle. As used herein, an immunogenic composition is a composition which elicits an immune response in a mammal to whom the composition is administered. The elicited immune response can be humoral or cell-mediated. As used herein, a vaccine composition is a composition which elicits an immune response in a mammal to whom the composition is administered and which protects the mammal from subsequent challenge or infection with the antigen of the composition or with a related organism.

As used herein, "protection", such as protection against RSV, refers to generation of an immune response in the vertebrate (e.g., mammal) which is protective (partially or totally) against manifestations of the disease caused by the antigen in the composition or a related organism, e.g., RSV. A vertebrate that is protected against disease caused by the RSV virus may be infected with RSV, but to a lesser degree than would occur without immunization; may be infected with RSV, but does not exhibit disease symptoms; or may be infected with RSV, but exhibits fewer disease symptoms than would occur without immunization. Alternatively, the vertebrate that is protected against disease caused by RSV may not become infected with the RSV virus at all, despite exposure to the virus.

The antigen component of the composition can be selected from virtually any antigen, antigenic determinant or hapten of medical or veterinary interest, and particularly for those antigens for which an increase in immunogenicity (e.g., CTL response) is desired. For example, the antigen may be in the form of purified or partially purified antigen derived from bacteria, viruses, rickettsia, fungi, parasites or their products, or extracts of bacteria, viruses, rickettsia fungi or parasites, or the antigen may be an allergen such as pollens, dusts, danders, or extracts of the same. The antigen may also be in the form of a poison or a venom derived from poisonous insects or reptiles. Preferably the antigen will be in the form in which its toxic or virulent properties have been reduced or destroyed and which when introduced into a suitable host in the composition of the invention will either induce active immunity by the production therein of antibodies against the specific microorganisms, extract or products of microorganisms used in the preparation of the antigen, or, in the case of allergens, will aid in alleviating the symptoms of the allergy due to the specific allergen. The antigens can be used either singly or in combination; for example, multiple bacterial antigens, multiple viral antigens, multiple mycoplasmal antigens, multiple rickettsial antigens, multiple fungal antigens, multiple parasitic antigens, multiple bacterial or viral toxoids, multiple allergens or combinations of any of the foregoing products can be combined with the adjuvant composition of this invention.

The combinations of adjuvants of this invention are suitable for use in immunogenic compositions containing a wide variety of antigens from a wide variety of pathogenic microorganisms, including but not limited to those from viruses, bacteria, fungi or parasitic microorganisms which infect humans and non-human vertebrates, or from a cancer cell or tumor cell. The antigen may comprise peptides or polypeptides derived from proteins, as well as fragments of any of the following: saccharides, proteins, poly- or oligonucleotides, cancer or tumor cells, or other macromolecular components. In some instances, more than one antigen is included in the immunogenic composition.

Desirable viral vaccines containing the adjuvant combinations of this invention include those directed to the prevention and/or treatment of disease caused by, without limitation, Human immunodeficiency virus, Respiratory syncytial virus, Parainfluenza virus types 1-3, Influenza virus, Herpes simplex virus, Human cytomegalovirus, Hepatitis A virus, Hepatitis B virus, Hepatitis C virus, Human papillomavirus, poliovirus, rotavirus, caliciviruses, Measles virus, Mumps virus, Rubella virus, adenovirus, rabies virus, canine distemper virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses.

Desirable bacterial vaccines containing the adjuvant combinations of this invention include those directed to the prevention and/or treatment of disease caused by, without limitation, Haemophilus influenzae (both typable and nontypable), Haemophilus somnus, Moraxella catarrhalis, Streptococcus pneumoniae, Streptococcus pyogenes, Streptococcus agalactiae, Streptococcus faecalis, Helicobacterpylori, Neisseria meningitidis, Neisseria gonorrhoeae, Chlamydia trachomatis, Chlamydia pneumoniae, Chlamydia psittaci, Bordetella pertussis, Salmonella typhi, Salmonella typhimurium, Salmonella choleraesuis, Escherichia coli, Shigella, Vibrio cholerae, Corynebacterium diphtheriae, Mycobacterinm tuberculosis, Mycobacterium aviumMycobacterium intracellulare complex, Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae and Mycoplasma gallisepticum. In one embodiment, the antigen is the P4 protein or functional portion thereof of non-typable Haemophilus influenzae.

Desirable vaccines against fungal pathogens containing the adjuvant combinations of this invention include those directed to the prevention and/or treatment of disease caused by, without limitation, Aspergillis, Blastomyces, Candida, Coccidiodes, Cryptococcus and Histoplasma.

Desirable vaccines against parasites containing the adjuvant combinations of the invention include those directed to the prevention and/or treatment of disease caused by, without limitation, Leishmania major, Ascaris, Trichuris, Giardia, Schistosoma, Cryptosporidiun, Trichomonas, Toxoplasma gondii and Pneumocystis carinii.

Desirable vaccines for eliciting a therapeutic or prophylactic anti-cancer effect in a vertebrate host, which contains the adjuvant combinations of this invention, include those utilizing a cancer antigen or tumor-associated antigen including, without limitation, prostate specific antigen, carcinoembryonic antigen, MUC-1, Her2, CA-125 and MAGE-3.

Desirable vaccines for moderating responses to allergens in a vertebrate host, which contain the adjuvant combinations of this invention, include those containing an allergen or fragment thereof. Examples of such allergens are described in U.S. Pat. No. 5,830,877 and published International Patent Application No. WO 99/51259, which are incorporated herein by reference, and include pollen, insect venoms, animal dander, fungal spores and drugs (such as penicillin). The vaccines interfere with the production of IgE antibodies, a known cause of allergic reactions.

Desirable vaccines for preventing or treating disease characterized by amyloid deposition in a vertebrate host, which contain the adjuvant combinations of this invention, include those containing portions of the amyloid peptide protein (APP). This disease is referred to variously as Alzheimer's disease, amyloidosis or amyloidogenic disease. The β-amyloid peptide (also referred to as AP peptide) is a 42 amino acid fragment of APP, which is generated by processing of APP by the β and γ secretase enzymes, and has the following sequence:

Asp Ala Glu Phe Arg His Asp Ser Gly Tyr Glu Val His His Gln Lys Leu Val Phe Phe Ala Glu Asp Val Gly Ser Asn Lys Gly Ala Ble Ile Gly Leu Met Val Gly Gly Val Val Ile Ala (SEQ ID NO: 1).

In some patients, the amyloid deposit takes the form of an aggregated Aβ peptide. Surprisingly it has now been found that administration of isolated Aβ peptide induces an immune response against the Aβ peptide component of an amyloid deposit in a vertebrate host (published International Patent Application No. WO 99/27944). Thus the vaccines of this invention include the adjuvant combinations of this invention plus Aβ peptide, as well as fragments of Aβ peptide and antibodies to Aβ peptide or fragments thereof. One such fragment of Aβ peptide is the 28 amino acid peptide having the following sequence (U.S. Pat. No. 4,666,829):

Asp Ala Glu Phe Arg His Asp Ser Gly Tyr Glu Val His His Gln Lys Leu Val Phe Phe Ala Glu Asp Val Gly Ser Asn Lys (SEQ ID NO: 2).

In a preferred embodiment the antigen is a respiratory syncytial virus antigen. Respiratory syncytial virus (RSV), a negative strand virus of the paramyxoviridae family, is a major cause of lower pulmonary tract disease, particularly in young children and infants. RSV contains two prominent outer envelope glycoproteins, fusion (F) protein and attachment (G) protein, that are important for viral infectivity and thus serve as reasonable targets for the design of a subunit vaccine to RSV. Although the invention is exemplified herein with reference to the RSV F protein antigen, it is understood that the invention is not limited to the use of RSV F protein antigens in the compositions of the invention.

The wild type (native) nucleotide and amino acid sequences of the RSV F protein are known in the art (Collins et al., *Proc. Natl. Acad. Sci (USA)* 81:7683-7687 (1984); U.S. Pat. No. 5,639,853; U.S. Pat. No. 5,723,130). RSV proteins suitable for use in the invention include the complete RSV F protein as well as functional portions of the RSV F protein. For example, a functional portion can be a portion of the protein which retains the ability to induce an antibody response when administered to a mammal. Examples of such immunogenic portions are polypeptides comprising amino acid positions 283-315, 289-315 and 294-299 of the RSV F protein. These regions include an epitope of the RSV F protein which elicits both neutralizing and antifusion antibodies (Paradiso et al. U.S. Pat. No. 5,639,853). Alternatively, an RSV F protein in its native dimeric form (140 kD) may be used (Paradiso et al., U.S. Pat. No. 5,223,254).

The F proteins and polypeptides of the invention can be partially or substantially purified (e.g., purified to homogeneity), and/or is substantially free of other proteins. Alternatively, the F protein or polypeptide of the invention can be chemically synthesized or recombinantly produced using methods known in the art (see, for example, Broach, et al., *Experimental Manipulation of Gene Expression*, ed. M. Inouye (Academic Press, 1983) p. 83; *Molecular Cloning: A Laboratory Manual,* 2nd Ed., ed. Sambrook et al. (Cold Spring Harbor Laboratory Press, 1989) Chapters 16 and 17). The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

Suitable RSV F proteins also include RSV proteins or portions there of having one or more amino acid alterations. As used herein, "alteration" and its derivatives is intended to mean a change in amino acid. Alterations include insertions, deletions and/or substitutions of one or more amino acids. For example, the alteration(s) can preferably be conservative amino acid changes or can preserve the three-dimensional configuration of the native F protein. Moreover, amino acids which are essential for the function of the F protein, particularly for immunogenicity, can be identified by methods known in the art. Particularly useful methods include identification of conserved amino acids, site-directed mutagenesis and alanine-scanning mutagenesis (for example, Cunningham and Wells, *Science* 244:1081-1085 (1989)), crystallization and nuclear magnetic resonance. The altered proteins or polypeptides produced by these methods can be tested for particular biologic activities, including immunogenicity and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306-1310 (1990)).

Protein antigens of the invention (e.g., the F protein or polypeptide) can also be fusion proteins comprising all or a portion of the protein amino acid sequence fused to an additional component. Additional components, such as radioisotopes and antigenic tags, can be selected to assist in the isolation and purification of the polypeptide or to extend the half life of the polypeptide. In one embodiment the protein antigen is the F protein or polypeptide which is a fusion protein comprising all or a portion of the F protein amino acid sequence fused to all or a portion of the RSV G protein amino acid sequence (Wertz et al., *Proc. Natl. Acad. Sci. USA* 92:4075-4079 (1985); Satake et al., *Nucl. Acids Res.* 13(21):7795-7810 (1985)).

The invention also relates to compositions comprising a nucleic acid molecule encoding the antigen (e.g., RSV F protein or polypeptide) and an effective amount of IL-12 and QS-21, along with an optional physiologically acceptable vehicle. Such a composition is referred to herein as an immunogenic nucleic acid composition or immunogenic DNA composition and is useful for the genetic immunization of vertebrates. The term, "genetic immunization", as used herein, refers to inoculation of a vertebrate, particularly a mammal, with a nucleic acid vaccine directed against a pathogenic agent, particularly RSV, resulting in elicitation of an immune response, and, preferably, in protection of the vertebrate against RSV. An "immunogenic nucleic acid composition" or "immunogenic DNA composition" as used herein is a nucleic acid construct comprising a nucleic acid molecule encoding a polypeptide antigen, particularly an RSV F protein or polypeptide. The nucleic acid construct can also include transcriptional promoter elements, enhancer elements, splicing signals, termination and polyadenylation signals, and other nucleic acid sequences. The immunogenic nucleic acid composition is administered with an effective amount of IL-12 and QS-21 as described herein.

The immunogenic nucleic acid composition can be produced by standard methods. For example, using known methods, a nucleic acid (e.g., DNA) encoding RSV F protein or polypeptide can be inserted into an expression vector to construct an immunogenic nucleic acid composition (see Maniatis et al. *Molecular Cloning, A Laboratory Manual,* 2nd edition, Cold Spring Harbor Laboratory Press (1989)). The individual vertebrate is inoculated with the immunogenic nucleic acid composition (i.e., the immunogenic nucleic acid composition is administered), using standard methods. The vertebrate can be inoculated subcutaneously, intravenously, intrapertoneally, intradermally, intramuscularly, topically, orally, rectally, nasally, buccally, vaginally, by inhalation spray, or via an implanted reservoir in dosage formulations containing conventional non-toxic, physiologically acceptable carriers or vehicles. Alternatively, the vertebrate is inoculated with the immunogenic nucleic acid composition through the use of a particle acceleration instrument (a "gene gun"). The form in which it is administered (e.g., capsule, tablet, solution, emulsion) will depend in part on the route by which it is administered. For example, for mucosal administration, nose drops, inhalants or suppositories can be used. In a particular embodiment, the nucleic acid construct is co-administered with a transfection-facilitating agent. In a preferred embodiment, the transfection-facilitating agent is bupivicaine (U.S. Pat. No. 5,593,972).

The amount of the antigen component or components of the immunogenic composition will vary depending in part upon the identity of the antigen, as well as upon the age, weight and medical condition of the host, as well as on the method of administration. Again, suitable doses are readily determined by persons skilled in the art. The number of doses and the dosage regimen for the immunogenic composition are also readily determined by persons skilled in the art. In some instances, the adjuvant properties of the combination of adjuvants may reduce the number of doses needed or the time course of the dosage regimen.

The immunogenic composition uses an adjuvant amount of the adjuvant composition. The term "adjuvant amount" as used herein refers to an amount of the adjuvant composition (or to the amount of adjuvant(s) other than QS-21 or IL-12) that is sufficient to elicit a humoral response, a CTL response, or both a humoral and a CTL response. Preferably the adjuvant amount is sufficient to enhance or modify the immune response for one or more antigens of the immunogenic composition. Preferably, when three or more adjuvants are used, the adjuvant amount is sufficient to enhance or modify the immune response for two or more antigens of the immunogenic composition.

The compositions of the invention can optionally comprise additional adjuvants such as vegetable oils or emulsions thereof, aluminum hydroxide, aluminum phosphate, surface active substances, e.g., hexadecylamin, octadecyl amino acid esters, octadecylamine, lysolecithin, dimethyldiotadecylammonium bromide, N,N-dicoctadecyl-N'-Nbis (2-hydroxyethyl-propane diamine), methoxyhexadecylglycerol, and pluronic polyols; polyamines, e.g., pyran, dextransulfate, poly IC, acrbopol; peptides, e.g., muramyl dipeptide, dimethylglycine, tuftsin; immune stimulating complexes; oil emulsions; lipopolysaccharides such as MPL® (3-O-deacylated monophosphoryl lipid A; RIBI ImmunoChem Research, Inc., Hamilton, Mont.); and mineral gels. The antigens of this invention can also be incorporated into liposomes, cochleates, biodegradable polymers such as poly-lactide, poly-glycolide and poly-lactide-co-glycides, or ISCOMS (immunostimulating complexes), and supplementary active ingredients may also be employed. In a preferred embodiment, the adjuvant, immunogenic, vaccine or pharmaceutical composition of the invention does not comprise substantial MPL®. As used herein, "substantial MPL®" is intended to mean an amount of MPL which imparts additional adjuvanticity to the composition. Alternatively, the adjuvant, immunogenic, vaccine or pharmaceutical composition can comprise MPL® in an amount less than about 1 µg, preferably less than about 0.5 µg, and more preferably less than about 1 Ug. The compositions of the present invention can also be administered in combination with bacterial toxins and their attenuated derivatives. The compositions of the invention can also be administered in combination with other lymphokines, including, but not limited to, IL-2, IL-3, IL-15, IFN-γ and GM-CSF.

The RSV F protein of the present invention can be coupled to another molecule in order to modulate or enhance the immune response. Suitable carrier proteins include bacterial toxins which are safe for administration to mammals and immunologically effective as carriers. Examples include pertussis, diphtheria, and tetanus toxoids and non-toxic mutant proteins (cross-reacting materials (CRM)), such as the non-toxic variant of diphtheria toxoid $CRM_{197}$. Fragments of the native toxins or toxoids, which contain at least one T-cell epitope, are also useful as carriers for antigens. Methods for preparing conjugates of antigens and carrier molecules are well known in the art and can be found, for example, in Dick and Burret, *Contrib Microbial Immunol.* 10:48-114 (Cruse J M, Lewis R E Jr, eds; Based, Krager (1989) and U.S. Pat. No. 5,360,897 (Anderson et al.). The antigen of the invention may also be adsorbed onto alum.

Compositions of the invention can comprise an optional physiologically or pharmaceutically acceptable vehicle or medium. The particular physiological medium can include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. The compositions may also be mixed with immunologically acceptable diluents or carriers in a conventional manner to prepare injectable liquid solutions or suspensions. A variety of routes of administration are possible including, but not limited to, oral, dietary, topical, vaginal, rectal, intradermal, transdermal (see, e.g., published international application WO 98/20734, incorporated herein by reference), parenteral (e.g., intravenous, intraarterial, intramuscular, subcutaneous injection), inhalation (e.g., intrabronchial, intraocular, intranasal or oral inhalation, intranasal drops), depending on the disease or condition to be treated. Other suitable methods of administration can also include rechargeable or biodegradable devices and slow release polymeric devices. The pharmaceutical compositions of this invention can also be administered as part of a combinatorial therapy with other agents.

The invention further relates to a method of eliciting an immune response to an antigen, such as an RSV antigen, comprising administering to a vertebrate, e.g., mammalian, host an immunologically effective amount of an immunogenic composition comprising a mixture of antigen and an effective amount of IL-12 and QS-21, and optionally comprising a physiologically acceptable vehicle. The invention also relates to a method of eliciting a humoral or CTL-mediated immune response in a vertebrate comprising administering to a vertebrate an immunologically effective amount of an immunogenic composition comprising a mixture of antigen and an effective amount of IL-12 and QS-21, and optionally comprising a physiologically acceptable vehicle. As used herein, an "immunologically effective" dose of the immunogenic composition is a dose which is suitable to elicit an immune response. The particular dosage will depend upon the age, weight composition can be optionally administered in a pharmaceutically or physiologically acceptable vehicle, such as physiological saline or ethanol polyols such as glycerol or propylene glycol. Vertebrates suitable for immunization as described herein include, but are not limited to, primates (e.g., humans), cows, sheep, goats, horses, dogs, cats, rabbits, guinea pigs, rats, mice or other bovine, ovine, equine, canine, feline, rodent or murine species.

The invention will be further described by the following non-limiting examples. The entire contents of all references, patents and patent applications cited herein are incorporated herein by reference.

EXAMPLES

The following examples are carried out using standard techniques, which are well known and routine to those of skill in the art, except where otherwise described in detail.

The following examples are presented for illustrative purpose, and should not be construed in any way limiting the scope of this invention.

Example 1

The Systemic Humoral Immune Responses of BALB/c Mice Vaccinated with RSV F Protein Co-Formulated with QS-21 and Recombinant (r) IL-12

The purpose of these experiments was to determine if immunization with RSV F protein formulated with QS-21 and recombinant IL-12 could elicit functional serum antibody titers that were greater than those achieved after immunization with either adjuvant alone. In the experiments native F protein was purified by ion exchange chromatography from Vero cells (ATCC No. CCL 81) infected with the A2 strain of RSV. The protein was greater than 95% pure as estimated by SDS-PAGE and antigen capture ELISA. QS-21 and rIL-12 were obtained from Aquila BioPharmaceuticals, Inc. (Worcester, Mass.) and Genetics Institute (Cambridge, Mass.), respectively. Naive female BALB/c mice (8-10 weeks of age) were obtained from Charles River Laboratories (Wilmington, Me.) and vaccinated intramuscularly on weeks 0 and 4 with natural F protein (3 µg/dose). The vaccines were prepared such that F protein was prepared with rIL-12 (F/rIL-12) in descending doses (1.0, 0.1, 0.01 µg) and co-formulated with a suboptimal dose of QS-21 (0.8 µg). Control mice were injected with F/rIL-12 without QS-21, F protein admixed with 20 or 0.8 µg QS-21, or F protein in PBS alone. Additional control mice were vaccinated after experimental infection ($\sim 2 \times 10^6$ pfu) with the A2 strain of RSV. Intranasal infections (0.05 ml) were performed under injectable anesthesia (ketamine (60 mg/kg) and xylazine (2-5 mg/kg), The Butler Co., Dublin Ohio).

The geometric mean serum IgG and neutralizing antibody titers (±1 standard deviation) were determined by endpoint ELISA and the plaque reduction neutralization test respectively, 2 weeks after secondary vaccination. The neutralizing titers were determined against the A2 strain of virus in the presence (+) or absence (−) of 5% (V/V) guinea pig serum (BioWhittaker, Walkersville, Md.) as a source of complement (C). The neutralization titers were calculated as the reciprocal of the serum dilution that showed 60% reduction (relative to the virus control) in the number of foci per well. Significant differences (<0.05) were determined after log transformation by Tukey-Kramer HSD multiple comparison using JMP® statistical discovery software (SAS Institute Inc., Cary, N.C.). There were 5 mice per group. All animals were housed in a facility accredited by the American Association for Accreditation of Laboratory Animal Care.

Results

The results shown in Table 1 confirmed previous data and demonstrated that vaccination with an optimal dose of QS-21 (20.0 µg) without IL-12 generated systemic humoral and cell-mediated immune responses that were similar in magnitude and function to that observed after experimental infection. The anti-F protein IgG1 and IgG2a titers and complement assisted neutralizing titers were significantly elevated 2 weeks after secondary vaccination. Vaccination with F protein admixed with a suboptimal dose of QS-21 (0.8 µg) without IL-12, on the other hand, resulted in serum antibody titers that were significantly less when compared to F/QS-21 (20.0 µg). The results also demonstrated that immunization with F/rIL-12 (0.01 to 1.0 µg) formulated in PBS alone (without QS-21) did not generate significant complement-assisted serum neutralizing titers.

In combination, the results indicated that QS-21 and rIL-12 formed a potent adjuvant formulation. A synergy between 0.8 µg QS-21 and rIL-12 was apparent for the generation of functional serum antibodies. Table 1 depicts antibody titers generated 2 weeks after secondary vaccination with F protein formulated with 0.8 µg QS-21 and rIL-12. The addition of 0.8 µg QS-21 to 1.0, 0.1 or 0.01 µg rIL-2 resulted in IgG2a and complement-assisted neutralization titers that were significantly greater than those generated after injection of F/rIL-12 without QS-21, or F/QS-21 (0.8 µg) alone. Moreover, the complement-assisted neutralization titers were not significantly different from that generated following experimental infection. When sera from mice vaccinated with F/rIL-12 (1.0 to 0.01 µg) plus 0.8 µg QS-21 were compared to those of mice immunized with F/rIL-12 without QS-21, significant differences in anti-F protein specific IgG1 titers were not observed. The synergy between rIL-12 and QS-21 for inducing RSV neutralizing titers was observed in three of four studies performed.

Example 2

The Determination of Antigen Dependent Killer Activity in the Spleens of BALB/c Mice Vaccinated with F Protein of Coformulated with QS-21 and rIL-12

The purpose of these experiments was to determine if immunization with F protein formulated with QS-21 and rIL-12 could elicit antigen dependent killer cell activities that were greater than those achieved after immunization with either adjuvant alone. In the experiments natural F protein was purified, and vaccines were prepared and administered to naive female BALB/c mice as described in Example 1. To determine the presence of antigen dependent killer cells, bulk splenocytes were collected 2 weeks after secondary immunization and cultured 6 days in the presence of syngenic RSV-infected stimulator cells. Thereafter the effector cells (serially diluted 3-fold in RPMI 1640 with 10% heat-inactivated fetal bovine sera) were tested against RSV-infected and control syngeneic target cells for antigen dependent killer cell activity in a standard $^{51}$Cr release assay. In FIG. 1F the effector to target ratio was 100:1. There were 5 mice per group.

Results

Figure 1A:
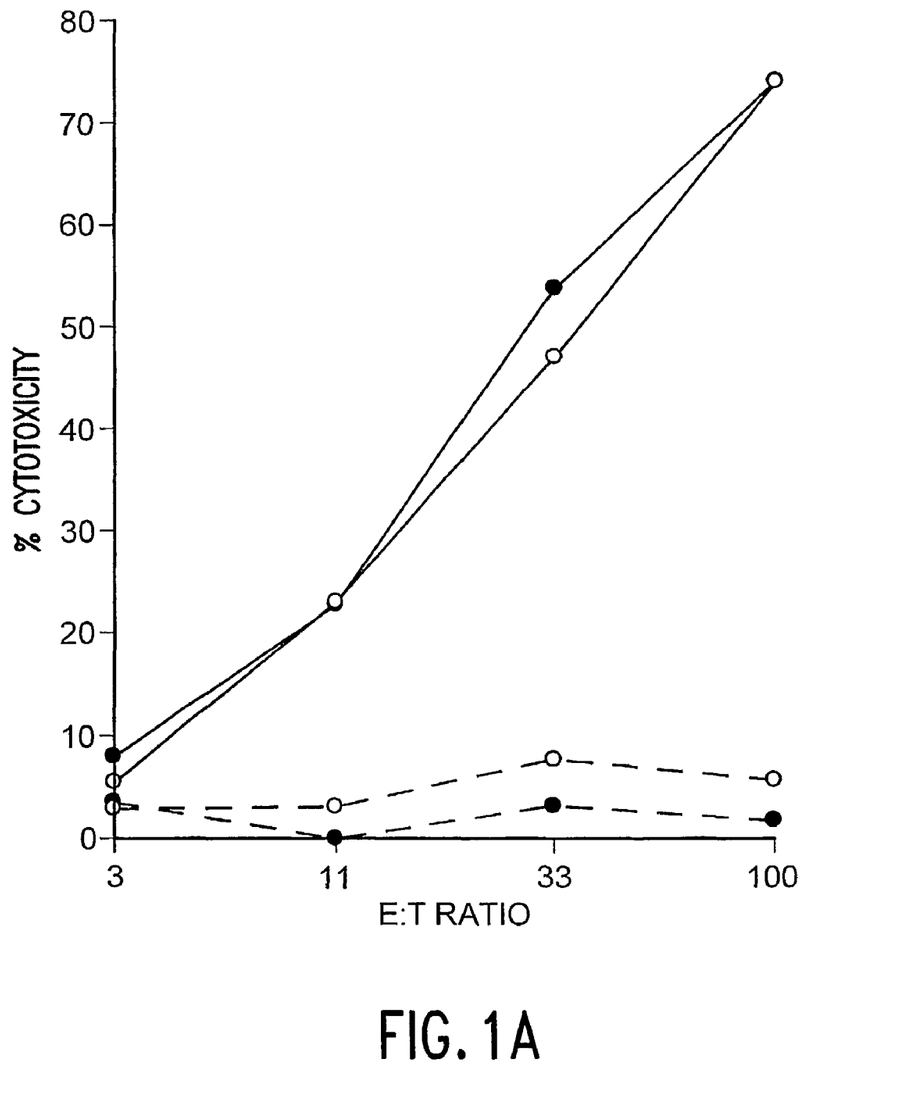
FIGS. 1A-1F show antigen dependent killer cell precursors in the spleens of BALB/c mice vaccinated with RSV F protein co-formulated with rIL-12 and QS-21.
Figure 1B:
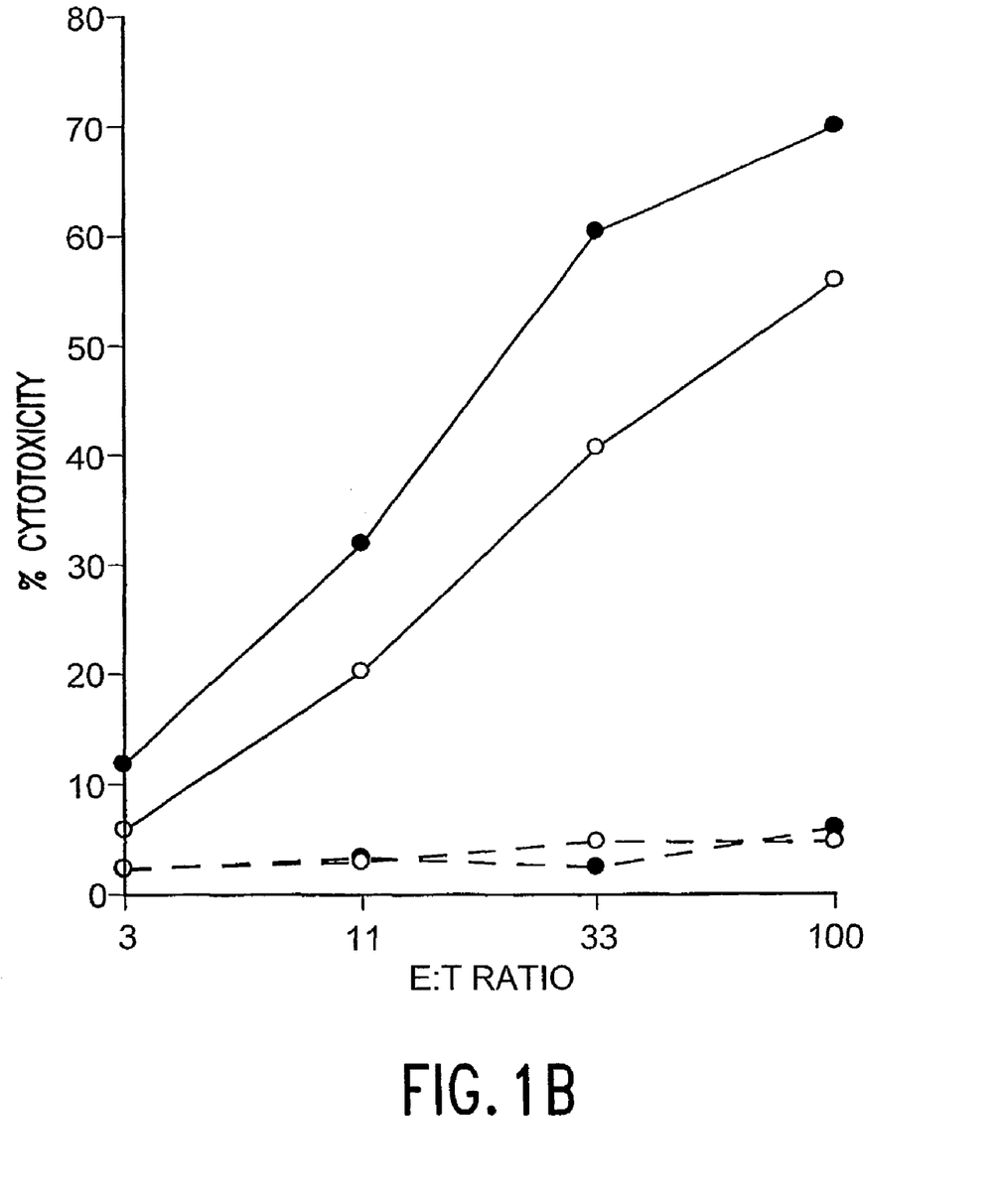
Figure 1C:
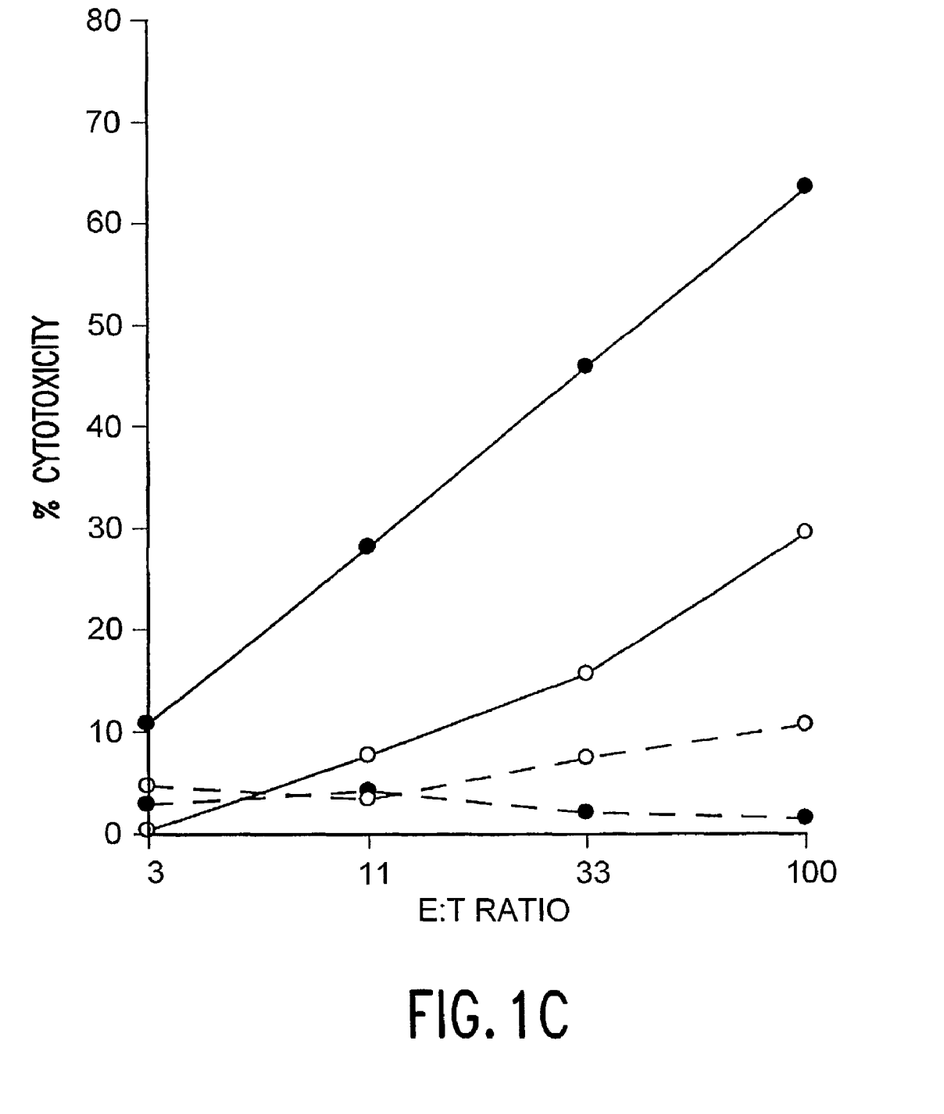
Figure 1D:
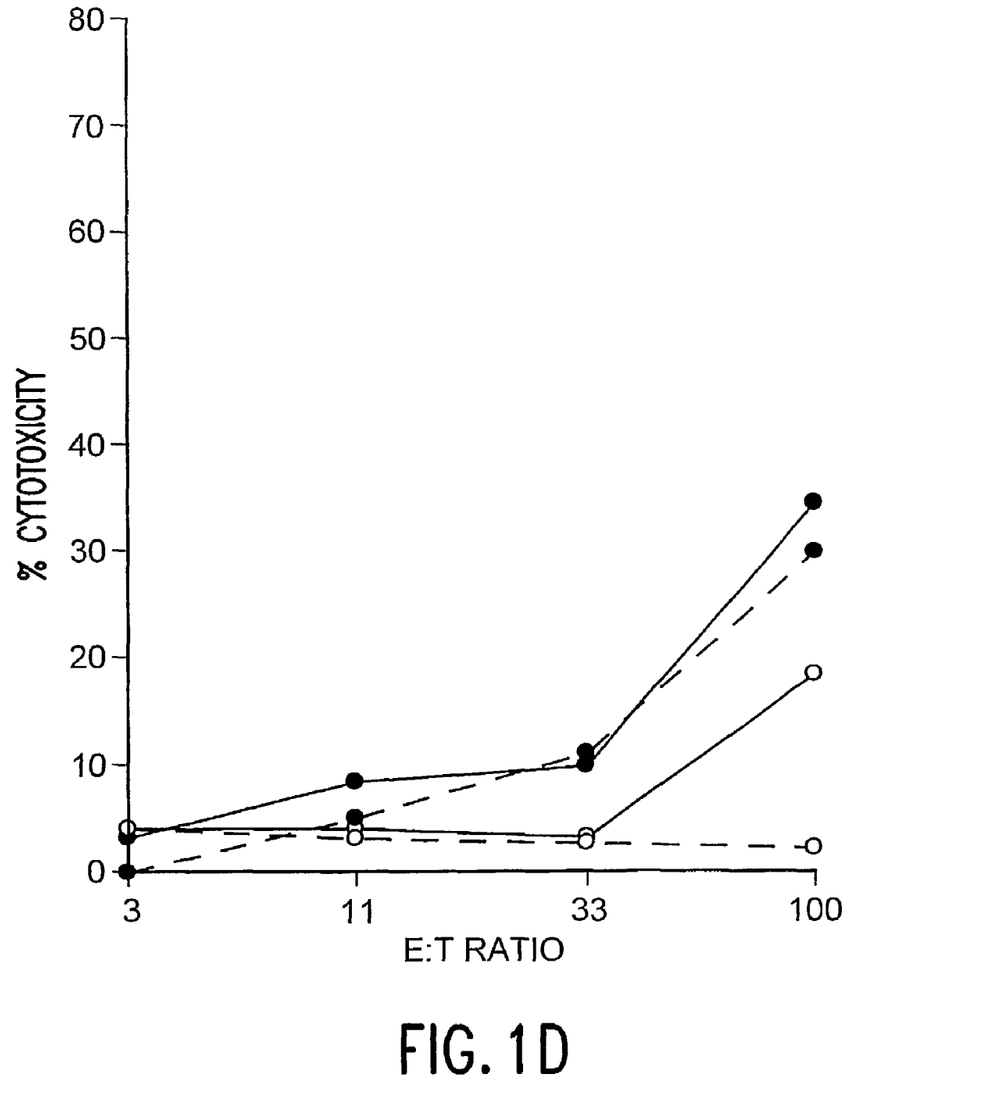
Figure 1E:
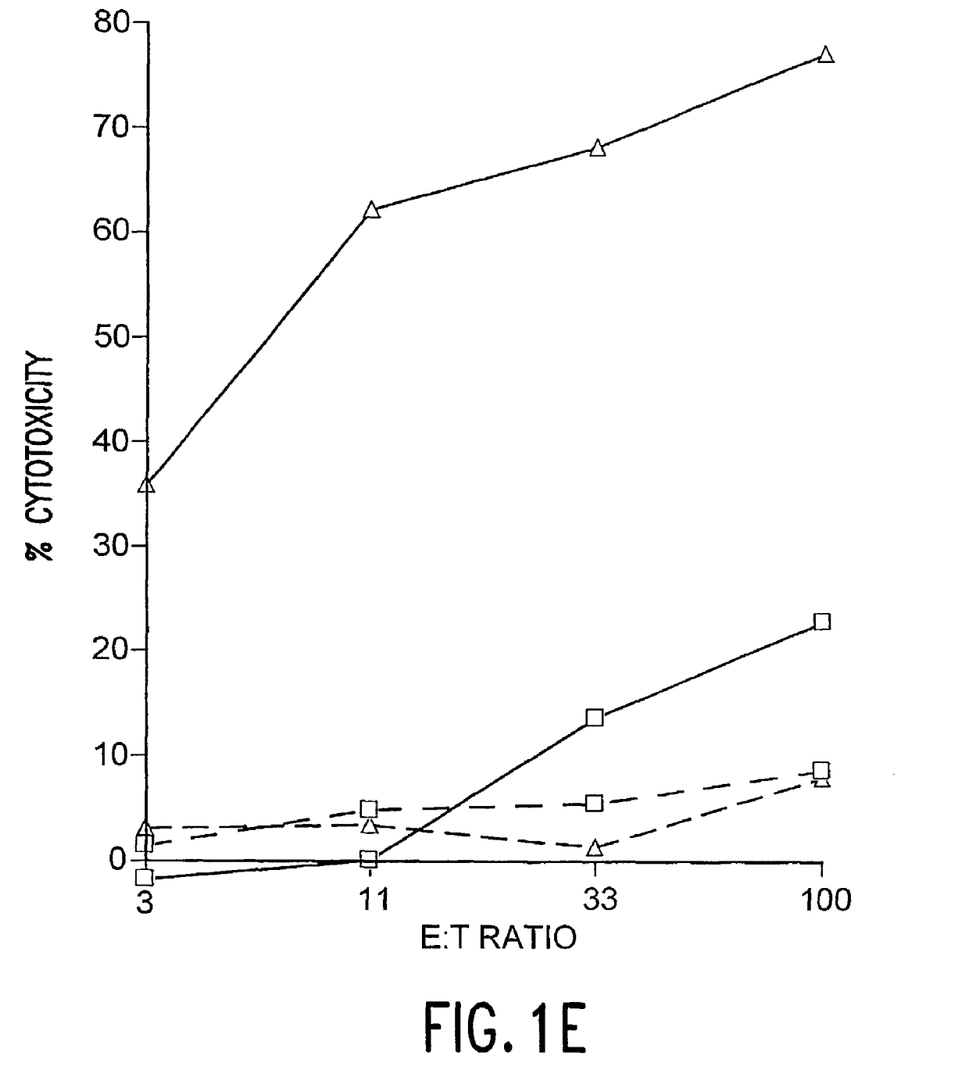
Figure 1F:
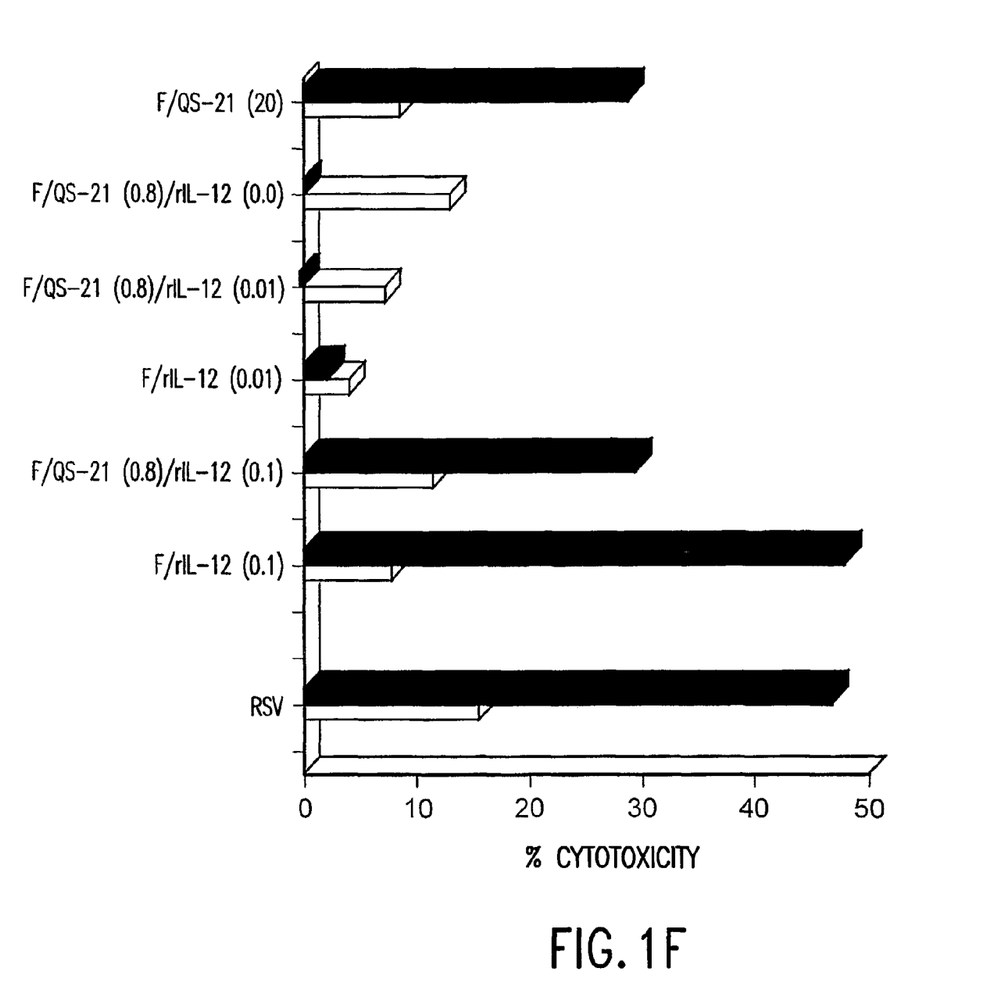

The results shown in FIGS. 1A-1F confirmed previously published data and demonstrated that immunization with F/QS-21 (20.0 µg) generated a remarkable increase in antigen dependent killer cell activity (FIGS. 1A and F). Vaccination with F protein admixed with a suboptimal dose of QS-21 (0.8 µg), on the other hand, did not elicit noteworthy antigen dependent killer cell activity (FIGS. 1C and F). The results also substantiated an earlier report which demonstrated that F/rIL-12 (0.01 to 1.0 µg) formulated in PBS alone did not generate detectable antigen dependent killer cells (FIGS. 1D and F).

In combination, however, the results indicated that QS-21 and rIL-12 formed a potent adjuvant formulation for F protein. The data demonstrated that 0.8 µg QS-21 was synergistic with 1.0 or 0.1 µg rIL-12 and enabled F protein to generate antigen dependent killer cell precursors in the spleens of BALB/c mice that were similar in level to that induced after experimental infection or vaccination with F/QS-21 (20 µg). The killer cell activity was respectively 5 and 3 times greater than that achieved after vaccination with F/rIL-12 (1.0 µg) (FIG. 1D) or, F/QS-21 (0.8 µg) (FIG. 1C), at the 33:1 effector to target ratio. FIG. 1F depicts data from a second experiment wherein 0.8 µg QS-21 was synergistic with 0.1 or 1.0 µg rIL-12 at the 100:1 effector to target ratio. The synergy between rIL-12 and QS-21 on the generation of functional cell mediated immune responses was not observed when 20.0 µg QS-21 was used in the vaccines (FIG. 1A). There did appear to be a trend towards synergy at the 4.0 µg QS-21 dose. Noteworthy killer cell activity was not observed in the spleens of mice vaccinated with F/AlOH. Cytolysis against syngeneic control targets not infected with RSV was not observed (FIG. 1). The synergy between rIL-12 and QS-21 for generating antigen dependent killer cell activity was observed in three of three studies performed.

TABLE 1

Serum antibody titers of BALB/c mice 2 weeks after secondary vaccination with F/rIL-12 plus QS-21.
Serum Antibody Titers ($Log_{10}$)

| Vaccine | | F Protein | | Neutralizing | |
|---|---|---|---|---|---|
| (µg) | QS-21 (µg) | IgG1 | IgG2a | (+) | (−) |
| F/rIL-12 (1.0) | 0.0 | 5.0 ± 0.3 | 4.2 ± 0.6$^c$ | 1.7 ± 0.5$^c$ | <1.3 |
| F/rIL-12 (1.0) | 0.8 | 5.8 ± 0.2 | 5.9 ± 0.3$^b$ | 3.8 ± 3$^b$ | 1.6 ± 0.2 |
| F/rIL-12 (0.1) | 0.0 | 5.4 ± 0.6 | 4.4 ± 0.6$^c$ | 2.5 ± 0.8$^c$ | <1.3 |
| F/rIL-12 (0.1) | 0.8 | 5.8 ± 0.1 | 5.7 ± 0.3$^b$ | 3.8 ± 0.4$^b$ | 1.8 ± 0.7 |
| F/rIL-12 (0.01) | 0.0 | 4.9 ± 0.4 | 3.7 ± 0.5$^c$ | 1.6 ± 0.5$^c$ | <1.3 |
| F/rIL-12 (0.01) | 0.8 | 5.7 ± 0.4 | 5.1 ± 0.3$^b$ | 3.1 ± 0.7$^b$ | 1.3 ± 0.1 |
| F/PBS | 20.0 | 6.3 ± 0.2 | 6.1 ± 0.4 | 3.7 ± 0.2$^b$ | 2.7 ± 0.2 |
| F/PBS | 0.8 | 5.2 ± 0.3$^a$ | 4.1 ± 0.6$^a$ | 1.9 ± 0.63$^a$ | 1.3 ± 0.1 |
| F/PBS | 0.0 | 3.4 ± 0.7 | 3.0 ± 0.2 | <1.3 | <1.3 |
| RSV | 0.0 | 5.0 ± 0.2 | 5.4 ± 0.1 | 3.7 ± 0.4 | 2.8 ± 0.6 |

$^a$P < 0.05 vs. IgG1, IgG2a, and C-assisted neutralizing antibody titers of mice vaccinated with F/PBS plus QS-21 (20.0 µg) or F/PBS.
$^b$P < 0.05 vs. IgG2a and C-assisted neutralizing titers from mice vaccinated with F/PBS QS-21 (0.8 µg) alone.
$^c$P < 0.05 vs. IgG2a and C-assisted neutralizing titers from comparable mice vaccinated with F/rIL-12 (1.0 to 0.01 µg) co-formulated with 0.8 µg QS-21.

Example 3

The Effect of an Adjuvant Comprised of QS-21 and rIL-12 on the Systemic Humoral Immune Responses Elicited by RSV G Protein, an Antigen Prone to Induce Th2 Helper T Cells The purpose of this experiment was to determine the adjuvant properties of rIL-12 plus QS-21 on humoral immune responses elicited by viral antigens prone to induce Th2 helper T cell responses. To that end, the effect of rIL-12 on the immune responses induced by natural G protein co-formulated with a suboptimal dose (0.8 µg) of QS-21 was investigated. In the experiment naïve female BALB/c mice (7-10 weeks of age) were primed intramuscularly with 1 µg natural G protein. The protein was purified via immunoaffinity chromatography from Vero cells infected with the A2 strain RSV and was greater than 95% pure as estimated by SDS PAGE electrophoresis. The protein was prepared in PBS alone, admixed with a suboptimal dose (0.8 µg) of QS-21 or admixed with a suboptimal dose (0.8 µg) of QS-21 plus 10 fold ascending doses of murine rIL-12 (0.01, 0.1, or 1.0 µg rIL-12). Control mice were primed with either 3 µg F or 1 µg G-protein formulated with an optimal dose (20.0 µg) of QS-21.

Sera were collected 4 weeks after primary vaccination for the determination (by ELISA) of geometric mean endpoint IgG antibody titers. Geometric mean serum neutralizing antibody titers were ascertained by the plaque reduction neutralization test against the A2 strain of virus. The neutralizing titers were determined in the presence (+) or (−) absence of 5% guinea pig sera as a source of complement (C). The neutralization titers were calculated as the reciprocal of the serum dilution that showed 60% reduction (relative to the virus control) in the number of foci per well. Significant differences (p<0.05) were determined after log transformation by Tukey-Kramer HSD multiple comparison test using JMP® statistical software (SAS Institute Inc., Cary, N.C.). For statistical analyses of IgG, endpoint titers less than 100 were assigned a value of 50.

Results

RSV G protein has been extensively studied and shown to be a potent inducer of Th2 helper T cell responses in BALB/c mice. Because rIL-12 can synergize with a suboptimal dose (0.8 µg) of QS-21 and elevate the Th1 helper T cell responses elicited by RSV F protein (TABLE 1 & FIG. 1), the effect of rIL-12 on the elicited by an antigen (G protein) that elicits Th2 T cell responses was investigated. It is known that QS-21 does not diminish the dominance of Th2 helper T cell responses induced by G protein. In the experiment the resultant serum anti-G protein IgG1 and IgG2a titers were respectively used to monitor the effects of rIL-12 on the generation of Th2 and Th1 helper T cell responses. The data shown in TABLE 2 demonstrated that 0.01 µg rIL-12 restored the adjuvant properties of suboptimal dose (0.8 µg) of QS-21 and induced anti-G protein IgG1 titers. The IgG1 titers were elevated when compared to G/PBS and in addition, not significantly different from those elicited after vaccination with an optimal dose (20.0 µg) of QS-21. At doses of rIL-12 greater than 0.01 µg, no significant differences in anti-G protein IgG1 titers were observed. The addition of 0.01 to 1.0 µg rIL-12 to G/QS-21 (0.8 µg) did not affect the generation of IgG2a titers. In addition, all neutralizing titers that were determined in the presence of complement were undetectable and less than $log_{10}$ 1.3. The only exception were sera from mice vaccinated with G protein plus an optimal dose (20.0 µg) of QS-21 (neutralization titer=$log_{10}$ 1.7). Thus, the data confirmed that rIL-12 could also restore the capacity of a suboptimal dose (0.8 µg) of QS-21 to adjuvant responses against antigens prone to elicit Th2 helper T cell responses.

TABLE 2

The ability of rIL-12 to restore the adjuvant properties of a suboptimal dose of QS-21 elicit serum IgG1 titers against natural G protein in BALB/c mice 4 weeks after primary vaccination.

| Vaccine (µg)$^‡$ | rIL-12 (µg) | Anti-G Protein Serum Titers ($log_{10}$)$^†$ | | |
|---|---|---|---|---|
| | | IgG | IgG1 | IgG2a |
| G/PBS | 0.0 | 3.4 ± 0.7 | <2.0 | 2.6 ± 0.9 |
| G/QS-21 (0.8) | 0.0 | 3.3 ± 0.5 | 2.3 ± 0.8 | 2.1 ± 0.9 |
| G/QS-21 (0.8) | 0.01 | 3.2 ± 0.9 | 2.8 ± 0.7$^a$ | 1.9 ± 0.5 |
| G/QS-21 (0.8) | 0.1 | 2.8 ± 1.2 | 2.1 ± 0.9 | 2.3 ± 0.9 |
| G/QS-21 (0.8) | 1.0 | 3.5 ± 0.8 | 2.5 ± 0.7 | 2.5 ± 0.9 |

TABLE 2-continued

The ability of rIL-12 to restore the adjuvant properties of a suboptimal dose of QS-21 elicit serum IgG1 titers against natural G protein in BALB/c mice 4 weeks after primary vaccination.

| Vaccine (µg)[‡] | rIL-12 (µg) | Anti-G Protein Serum Titers ($\log_{10}$)[†] | | |
|---|---|---|---|---|
| | | IgG | IgG1 | IgG2a |
| G/QS-21 (20) | 0.0 | 4.5 ± 0.4 | 3.8 ± 0.2[b] | 3.3 ± 0.6 |
| G/QS-21 (20) | 1.0 | 3.5 ± 0.3 | 2.4 ± 0.7 | 2.7 ± 0.6 |

[‡]BALB/c mice were primed with 1.0 µg G protein admixed with 0.8 µg QS-21 plus ascending doses of murine rIL-12 (0.0 to 1.0 µg/dose). Additional control mice were primed with G protein prepared in PBS alone, admixed with 20.0 µg QS-21, or 20.0 µg QS-21 plus 1.0 µg IL-12.
[†]The geometric mean serum endpoint IgG titers ($\log_{10}$ ± 1 standard deviation) were determined by ELISA. There were 5 mice per group.
[a]p > 0.05 vs. IgG1 antibody titers from mice primed with G/QS-21 (20.0 µg) without rIL-12.
[b]p < 0.05 vs. IgG1 antibody titers from all mice except those primed with G/QS-21 (0.8 µg) plus 0.01 µg rIL-12.

Example 4

The Ability of rIL-12 to Restore the Capacity of RSV G Protein Co-Formulated with QS-21 to Prime BALB/c Mice for Pulmonary Eosinophilia The purpose of this experiment was to ascertain what effect an adjuvant comprised of rIL-12 and QS-21 would have on the properties of natural G protein to prime mice for pulmonary eosinophilia after challenge. Eosinophilia is dependent on CD4[+] helper Th2 cells and the cytokine, interleukin-5. In the experiment naïve female BALB/c mice (7-10 weeks of age) were primed intramuscularly with 1 µg natural G protein. The protein was purified via immunoaffinity chromatography from Vero cells infected with the A2 strain of RSV and greater than 95% pure as estimated by SDS PAGE. The protein was prepared in PBS alone, admixed with a suboptimal dose of QS-21 (0.8 µg/dose), or admixed with a suboptimal dose of QS-21 (0.8 µg/dose) plus 10-fold ascending doses of murine rIL-12 (0.01, 0.1, or 1.0 µg rIL-12). Control mice were primed with either 3 µg F or 1 µg G protein admixed with an optimal dose (20.0 µg) QS-21.

The mice were subsequently challenged 4 weeks after primary vaccination. Intranasal challenges (0.05 ml) were performed under injectable anesthesia (ketamine and xylazine). Bronchoalveolar lavage (BAL) was performed 5 days thereafter. The relative percentage of eosinophils was ascertained as described after the examination of at least 400 leukocytes on slides stained with Diff-Quik (Dade International, Miami, Fla.). Significant differences (p<0.05) were determined after log transformation by Tukey-Kramer HSD multiple comparison test using JMP® statistical software (SAS Institute Inc., Cary, N.C.).

Results

The results shown in TABLE 3 depict the mean percent eosinophilia in the lungs 5 days after challenge of BALB/c mice primed with G/QS-21 (0.8 µg) co-formulated with ascending doses of rIL-12. The data indicated that rIL-12 enhanced the adjuvant properties of a suboptimal dose (0.8 µg) of QS-21 and facilitated the natural tendency of G protein to elicit Th2 helper T cell responses. As the amount of rIL-12 that was added to G/QS-21 (0.8 µg) was increased, pulmonary eosinophilia was statistically elevated to levels equivalent to those observed after vaccination with G protein co-formulated with an optimal dose (20.0 µg) of QS-21. Hence, the pulmonary eosinophilia of mice primed with G/QS-21 (0.8 µg) plus 1.0 µg rIL-12 was equivalent to that of mice primed with G/QS-21 (20.0 µg) after challenge. The data further demonstrated that 1.0 µg rIL-12 did not diminish the dominance of the Th2 helper T cell responses generated by G/QS-21 (20.0 µg). Immunization with F/QS-21 did not predispose BALB/c mice for pulmonary eosinophilia after challenge.

TABLE 3

The effect of rIL-12 on the capacity of G protein admixed with a suboptimal dose of QS-21 to generate Th2 helper T cell responses[†].

| Vaccine (µg) | rIL-12 (µg) | % EOSINOPHILS[‡] |
|---|---|---|
| G/PBS | 0.0 | 5 |
| G/QS-21 (0.8) | 0.0 | 2[a] |
| G/QS-21 (0.8) | 0.01 | 20 |
| G/QS-21 (0.8) | 0.1 | 20 |
| G/QS-21 (0.8) | 1.0 | 25[b] |
| G/QS-21 (20) | 0.0 | 40 |
| G/QS-21 (20) | 1.0 | 40[b] |
| F/QS-21 (20) | 0.0 | 2 |

[†]BALB/c mice were primed with 1 µg natural G protein prepared in PBS, admixed with 0.8 or 20 µg QS-21, or admixed with 0.8 µg QS-21 plus 10-fold ascending doses of murine rIL-12. Control mice were primed with 3 µg F admixed with QS-21. The mice were challenged with the A2 strain of RSV 4 weeks later. The mean relative percentages of eosinophils were determined 5 days after challenge following the examination of at least 400 leukocytes. There were 5 mice per group.
[‡]The numbers are the relative mean percent eosinophils. Statistical differences were determined after log transformation.
[a]p < 0.05 vs. percent eosinophils from mice primed with G/QS-21 (0.8 µg) plus 0.01 to 1.0 µg IL-12 and G/QS-21 (20.0 µg). p > 0.05 vs. G/PBS and F/QS-21.
[b]p > 0.05 vs. G/QS-21 (20.0 µg) without rIL-12.

Example 5

The Effect of rIL-12 on the Systemic Humoral Immune Responses Elicited by Recombinant Non-Lipidated P4 Protein from Non-Typable Hemophilus influenzae Co-Formulated with QS-21

The purpose of this experiment was to confirm the effects of an adjuvant comprised of rIL-12 and QS-21 on humoral immune responses generated by bacterial antigens. To that end, the effects of rIL-12 on the immune responses induced by non-lipidated recombinant P4 (rP4) protein from non-typable Hemophilus influenzae when admixed with QS-21 was investigated. In the experiment naïve female BALB/c mice (7-10 weeks of age) were vaccinated subcutaneously on weeks 0 and 4 with 10 µg rP4 protein. The protein was prepared in PBS alone, admixed with a suboptimal dose (0.8 µg/dose) of QS-21, or admixed with a suboptimal dose (0.8 µg/dose) of QS-21 plus 10-fold ascending doses of murine rIL-12 (0.01, 0.1, or 1.0 µg rIL-12). Additional control mice were immunized with rP4 protein formulated with an optimal dose (20.0 µg) of QS-21 or aluminum phosphate (AlPO, 100.0 µg/dose) without rIL-12. Sera were collected 4 and 2 weeks after primary and secondary vaccination respectively for the determination (by ELISA) of geometric mean endpoint IgG titers. Significant differences (p<0.05) were determined after log transformation by Tukey-Kramer HSD multiple comparison test using JMP® statistical software.

Results

The results depicted in TABLE 4 demonstrated that rIL-12 could act together with a suboptimal dose of QS-21 and augment the systemic humoral immune responses generated by a bacterial antigen, the rP4 protein of non-typable *H. influenzae*. When compared to immunization with rP4/QS-21 (0.8 µg) without rIL-12, immunization with rP4/QS-21 (0.8 µg/dose) plus 0.01, 0.1, or 1.0 µg rIL-12 resulted in significantly greater serum anti-rP4 IgG2a titers 2 weeks after secondary vaccination. The IgG2a titers were also significantly greater than those generated following vaccination with rP4/AlPO. These titers were not significantly different from those of mice induced by rP4 protein admixed with an optimal dose (20.0 µg) QS-21 without rIL-12. The addition of 1.0 µg rIL-12 to rP4 protein admixed with a suboptimal dose of QS-21 also resulted in significantly increased IgG1 titers when compared to vaccination with rP4/PBS or rP4/AlPO. Thus the data confirmed that rIL-12 could augment the adjuvant properties of a suboptimal dose (0.8 µg) of QS-21 for both bacterial and viral antigens. There were no statistically significant differences in anti-rP4 IgG titers 4 weeks after primary vaccination.

TABLE 4

The effect of rIL-12 the ability of rP4 protein of non-typable *Hemophilus influenzae* co-formulated with a suboptimal dose of QS-21 elicit systemic humoral immune responses in BALB/c mice.

| Vaccine (µg)[†] | rIL-12 (µg) | Anti-rP4 IgG Titers[‡] | | |
|---|---|---|---|---|
| | | IgG | IgG1 | IgG2a |
| rP4/PBS | 0.0 | 6.1 ± 0.0 | 5.9 ± 0.1 | 4.7 ± 0.4 |
| rP4/QS-21 (0.8) | 0.0 | 6.4 ± 0.0 | 6.3 ± 0.1 | 5.0 ± 0.3 |
| rP4/QS-21 (0.8) | 0.01 | 6.6 ± 0.1 | 6.4 ± 0.3 | 5.9 ± 0.1[a] |
| rP4/QS-21 (0.8) | 0.1 | 6.7 ± 0.2 | 6.2 ± 0.2 | 6.2 ± 0.3[a] |
| rP4/QS-21 (0.8) | 1.0 | 7.0 ± 0.1[a] | 6.5 ± 0.2[b] | 6.2 ± 0.2[a] |
| rP4/QS-21 (20) | 0.0 | 6.9 ± 0.1 | 6.2 ± 0.3 | 6.3 ± 0.2[a] |
| rP4/AlPO (100) | 0.0 | 6.1 ± 0.2 | 6.0 ± 0.2 | 4.6 ± 0.3 |

[‡]The geometric mean IgG antibody titers ($\log_{10}$ ± 1 standard deviation) were determined by ELISA on sera collected 2 weeks after secondary vaccination. There were 5 mice per group.
[†]BALB/c mice were vaccinated subcutaneously on weeks 0 and 4 with 10.0 µg rP4 protein. The protein was formulated with QS-21 (0.8 µg) plus the indicated ascending amounts of recombinant rIL-12. Control mice were injected with rP4 prepared in PBS, admixed to QS-21 (20.0 µg/dose), or adsorbed to aluminum phosphate (AlPO, 100 µg/dose) without rIL-12.
[a]$p < 0.05$ vs. total IgG or IgG2a antibody titers from rP4/PBS, rP4/AlPO, and rP4/QS-21 (0.8) without rIL-12.
[b]$p < 0.05$ vs. total IgG1 antibody titers from rP4/PBS and rP4/AlPO.

Example 6

The Effects of rIL-12 on the Systemic Humoral Immune Responses Generated by Recombinant Lipidated P4 Protein from Non-Typable *Hemophilus influenzae* Admixed with QS-21

The purpose of this experiment was to determine the effects of an adjuvant comprising rIL-12 and QS-21 on the humoral immune responses elicited by a lipidated bacterial antigen. To that end, the effect of rIL-12 and QS-21 on the immune responses induced by recombinant lipidated P4 (rLP4) protein from non-typable *Hemophilus influenzae* was tested. In the experiment naïve female BALB/c mice (8-10 weeks of age) were vaccinated intramuscularly on weeks 0 and 4 with 5 µg rLP4 protein. The protein was prepared in PBS alone, admixed with 5 fold ascending doses (0.8-20.0 µg) of QS-21, 10-fold ascending doses of murine rIL-12 (0.01, 0.1, or 1.0 µg rIL-12), or the indicated combinations of QS-21 and rIL-12. Sera were collected 4 and 2 weeks after primary and secondary vaccination respectively for the determination (by ELISA) of geometric mean endpoint IgG titers. Significant differences ($p<0.05$) were determined after log transformation by Tukey-Kramer HSD multiple comparison test using JMP® statistical software.

Results

TABLES 5 and 6 respectively depict anti-rLP4 IgG titers 4 and 2 weeks after primary and secondary vaccination. The results demonstrated that QS-21 or rIL-12 alone were excellent adjuvants for enhancing the generation of humoral immune responses against rLP4. This was best observed by the increased anti-rLP4 IgG2a titers. For example, 4 weeks after immunization the titers of mice primed with rLP4/rIL-12 (0.01 µg) or rLP4/rIL-12 (1.0 µg) were respectively increased 10 and 100 fold when compared to the sera from mice injected with rLP4 prepared in PBS alone (TABLE 5). Likewise, the IgG2a titers of mice primed with rLP4/QS-21 (4.0 µg) or rLP4/QS-21 (20.0 µg) were augmented 100 fold (TABLE 5). Similar results were observed 2 weeks after secondary vaccination

TABLE 5

The serum IgG titers of BALB/c mice 4 weeks after primary immunization with rLP4 protein co-formulated with QS-21 plus IL-12[†].

| Antigen | Adjuvants (µg) | Anti-rLP4 Protein ($\log_{10}$)[a] | |
|---|---|---|---|
| | | IgG1 | IgG2a |
| rLP4 | QS-21 (20) | 4.9 ± 0.5 | 5.0 ± 0.3 |
| rLP4 | QS-21 (20) + rIL-12 (0.01) | 4.1 ± 0.4 | 5.1 ± 0.4 |
| rLP4 | QS-21 (20) + rIL-12 (0.1) | 4.3 ± 0.3 | 5.8 ± 0.6 |
| rLP4 | QS-21 (20) + rIL-12 (1.0) | 4.2 ± 0.9 | 5.0 ± 1.5 |
| rLP4 | QS-12 (4) | 5.3 ± 0.4 | 4.7 ± 0.5 |
| rLP4 | QS-21 (4) + IL-12 (0.01) | 5.1 ± 0.4 | 4.7 ± 0.5 |
| rLP4 | QS-21 (4) IL-12 (0.1) | 4.5 ± 0.5 | 5.0 ± 0.5 |
| rLP4 | QS-21 (4) + IL-12 (1.0) | 4.8 ± 0.5 | 5.5 ± 1.1 |
| rLP4 | QS-21 (0.8) | 3.3 ± 0.6 | 2.4 ± 0.8 |
| rLP4 | QS-21 (0.8) + rIL-12 (0.01) | 3.7 ± 0.7 | 2.7 ± 0.7 |
| rLP4 | QS-21 (0.8) + rIL-12 (0.1) | 3.8 ± 0.5 | 2.9 ± 0.3 |
| rLP4 | QS-21 (0.8) + rIL-12 (1.0) | 3.6 ± 0.3 | 3.8 ± 0.7 |
| rLP4 | None | 3.6 ± 0.4 | 2.1 ± 0.4 |
| rLP4 | rIL-12 (0.01) | 3.7 ± 0.9 | 3.1 ± 0.4 |
| rLP4 | rIL-12 (0.1) | 4.0 ± 0.4 | 3.2 ± 0.3 |
| rLP4 | rIL-12 (1.0) | 4.3 ± 0.1 | 4.0 ± 0.7 |

[†]BALB/c mice were primed intramuscularly with 5 µg rLP4 protein prepared in PBS alone, admixed with the indicated doses (0.8-20.0 µg) of QS-21, 10-fold ascending doses of murine rIL-12 (0.01, 0.1, or 1.0 µg rIL-12/), or combinations of QS-21 and rIL-12.
[a]The numbers are the geometric mean endpoint antibody titers ±1 standard deviation. There were 5 mice per group.

TABLE 6

The serum IgG titers of BALB/c mice 2 weeks after secondary immunization with rLP4 protein co-formulated with QS-21 plus IL-12[†]

| Antigen | Adjuvants (µg) | Anti-rLP4 IgG Titers ($\log_{10}$)[a] | |
|---|---|---|---|
| | | IgG1 | IgG2a |
| rLP4 | QS-21 (20) | 6.8 ± 0.4 | 7.0 ± 0.3 |
| rLP4 | QS-21 (20) + rIL-12 (0.01) | 6.6 ± 0.4 | 7.3 ± 0.4 |
| rLP4 | QS-21 (20) + rIL-12 (0.1) | 6.6 ± 0.4 | 7.2 ± 0.5 |
| rLP4 | QS-21 (20) + rIL-12 (1.0) | 6.3 ± 0.3 | 7.2 ± 0.3 |
| rLP4 | QS-21 (4) | 6.2 ± 0.5 | 6.6 ± 0.5 |
| rLP4 | QS-21 (4) + rIL-12 (0.01) | 5.5 ± 0.1 | 6.2 ± 0.5 |
| rLP4 | QS-21 (4) + rIL-12 (0.1) | 5.8 ± 0.3 | 6.3 ± 0.2 |
| rLP4 | QS-21 (4) + rIL-12 (1.0) | 5.9 ± 0.3 | 7.4 ± 0.5 |
| rLP4 | QS-21 (0.8) | 5.6 ± 0.5 | 4.5 ± 0.6 |
| rLP4 | QS-21 (0.8) + rIL-12 (0.01) | 5.3 ± 1.0 | 4.3 ± 0.5 |
| rLP4 | QS-21 (0.8) + rIL-12 (0.1) | 5.2 ± 0.2 | 4.8 ± 0.8 |
| rLP4 | QS-21 (0.8) + rIL-12 (1.0) | 5.4 ± 0.3 | 6.0 ± 0.7 |
| rLP4 | None | 5.5 ± 0.3 | 4.4 ± 0.5 |
| rLP4 | rIL-12 (0.01) | 4.6 ± 0.6 | 4.0 ± 0.4 |

TABLE 6-continued

The serum IgG titers of BALB/c mice 2 weeks after secondary immunization with rLP4 protein co-formulated with QS-21 plus IL-12[†]

| Antigen | Adjuvants (μg) | Anti-rLP4 IgG Titers (Log$_{10}$)[a] | |
|---|---|---|---|
| | | IgG1 | IgG2a |
| rLP4 | rIL-12 (0.1) | 5.0 ± 0.3 | 4.3 ± 1.0 |
| rLP4 | rIL-12 (1.0) | 5.3 ± 0.6 | 5.9 ± 0.9 |

[†]BALB/c mice were vaccinated intramuscularly on weeks 0 and 4 with 5 μg rLP4 protein. The protein prepared in PBS alone, admixed with the indicated doses (0.8-20.0 μg) of QS-21, 10-fold ascending doses of murine rIL-12 (0.01, 0.1, or 1.0 μg rIL-12/), or combinations of QS-21 and rIL-12.
[a]The numbers are the geometric mean endpoint IgG titers ±1 standard deviation. There were 5 mice per group.

While this invention has been particularly shown and described with references to preferred embodiments thereof, it will be understood by those skilled in the art that various changes in form and details may be made therein without departing from the scope of the invention encompassed by the appended claims.

What is claimed is:

1. An immunogenic composition comprising:
   (a) a bacterial or viral antigen for which an increase in immunogenicity is desired, wherein said bacterial antigen is not lipidated,
   (b) a pharmaceutically acceptable vehicle, and
   (c) an adjuvant formulation that consists of a synergistic combination of 0.8 μg of QS-21 and 0.01 μg to 1.0 μg of IL-12.

2. The immunogenic composition of claim 1, wherein said IL-12 is recombinant human IL-12.

3. The immunogenic composition of claim 1, wherein the amount of IL-12 in the adjuvant formulation is 0.01 μg of IL-12.

4. The immunogenic composition of claim 1, wherein the amount of IL-12 in the adjuvant formulation is 0.05 μg of IL-12.

5. The immunogenic composition of claim 1, wherein the amount of IL-12 in the adjuvant formulation is 0.1 μg of IL-12.

6. The immunogenic composition of claim 1, wherein said antigen is a bacterial protein.

7. The immunogenic composition according to claim 6, wherein said antigen is P4 protein from non-typable *Haemophilus influenzae*.

8. The immunogenic composition of claim 1, wherein said antigen is a viral protein.

9. The immunogenic composition according to claim 8, wherein said antigen is respiratory syncytial virus F protein.

10. The immunogenic composition of claim 1, wherein the amount of IL-12 in the adjuvant formulation is 0.5 μg of IL-12.

11. The immunogenic composition of claim 1, wherein the amount of IL-12 in the adjuvant formulation is 1.0 μg of IL-12.

12. A method of eliciting an immune response to a bacterial or viral antigen for which an increase in immunogenicity is desired, wherein said bacterial antigen is not lipidated, comprising administering to a vertebrate a composition comprising:
   (a) said antigen,
   (b) a pharmaceutically acceptable vehicle, and (c) an adjuvant formulation that consists of a synergistic combination of 0.8 μg of QS-21 and 0.01 μg to 1.0 μg of IL-12.

13. The method of claim 12, wherein said IL-12 is recombinant human IL-12.

14. The method of claim 12, wherein the amount of IL-12 in the adjuvant formulation is 0.01 μg of IL-12.

15. The method of claim 12, wherein said antigen is a bacterial protein.

16. The method according to claim 15, wherein said antigen is P4 protein from non-typable *Haemophilus influenzae*.

17. The method of claim 12, wherein said antigen is a viral protein.

18. The method according to claim 17, wherein said antigen is respiratory syncytial virus F protein.

19. The method of claim 1, wherein the amount of IL-12 in the adjuvant formulation is 0.5 μg of IL-12.

20. The method of claim 12, wherein the amount of IL-12 in the adjuvant formulation is 1.0 μg of IL-12.

* * * * *

UNITED STATES PATENT AND TRADEMARK OFFICE
CERTIFICATE OF CORRECTION

PATENT NO. : 7,374,751 B1 Page 1 of 1
APPLICATION NO. : 10/311422
DATED : May 20, 2008
INVENTOR(S) : Gerald E. Hancock It is certified that error appears in the above-identified patent and that said Letters Patent is hereby corrected as shown below:

On the title page insert item (60), provisional application number 60/213,143, filed on June 22, 2000.

Signed and Sealed this

Twenty-eighth Day of October, 2008

JON W. DUDAS
*Director of the United States Patent and Trademark Office*